(12) United States Patent
Bothorel et al.

(10) Patent No.: US 8,670,521 B2
(45) Date of Patent: Mar. 11, 2014

(54) METHOD FOR GENERATING AN INTRAORAL VOLUME IMAGE

(75) Inventors: Sylvie Bothorel, Paris (FR); Edward R. Shellard, Atlanta, GA (US); Jean-Marc Inglese, Bussy Saint Georges (FR)

(73) Assignee: Carestream Health, Inc., Rochester, NY (US)

( * ) Notice: Subject to any disclaimer, the term of this patent is extended or adjusted under 35 U.S.C. 154(b) by 453 days.

(21) Appl. No.: 13/151,748

(22) Filed: Jun. 2, 2011

(65) Prior Publication Data

US 2012/0307965 A1   Dec. 6, 2012

(51) Int. Cl.
*A61B 6/14* (2006.01)

(52) U.S. Cl.
USPC .............................. 378/39; 378/205

(58) Field of Classification Search
USPC ................... 378/39, 40, 205, 62, 168
See application file for complete search history.

(56) References Cited

U.S. PATENT DOCUMENTS

| 7,269,241 | B2 | 9/2007 | Siltanen et al. | |
| 2003/0099328 | A1 | 5/2003 | Jensen et al. | |
| 2006/0285646 | A1 | 12/2006 | Unfors | |
| 2007/0001905 | A1 | 1/2007 | Eronen | |
| 2007/0019005 | A1 | 1/2007 | Eronen | |
| 2007/0127801 | A1 | 6/2007 | Kalke | |
| 2009/0028293 | A1* | 1/2009 | Wolfe | 378/62 |
| 2009/0060145 | A1 | 3/2009 | Tranchant et al. | |
| 2009/0207971 | A1 | 8/2009 | Uhde et al. | |
| 2009/0232275 | A1* | 9/2009 | Spartiotis et al. | 378/40 |

OTHER PUBLICATIONS

Yiheng Zhang et al., "A comparative study of limited-angle cone beam reconstruction methods for breast Tomosynthesis," Med. Phys., vol. 33, Issue 10, Oct. 2006, pp. 3781-3795.
International Search Report mailed on Nov. 30, 2012 for International Application No. PCT/US2012/034731, 2 pages.

* cited by examiner

*Primary Examiner* — Hoon Song

(57) ABSTRACT

A method for obtaining an intraoral x-ray image determines an initial spatial position and angular orientation of an x-ray source relative to a detector. A first x-ray image is obtained with the x-ray source at the initial spatial position and angular orientation and stored, associating the initial spatial position and angular orientation to the first x-ray image. A sequence repeats that calculates a next spatial position and angular orientation for the x-ray source, provides positional adjustment information between the x-ray source and detector for obtaining a next x-ray image, measures and records the actual spatial position and angular orientation of the x-ray source relative to the detector and obtains and stores the next x-ray image at the measured spatial position and angular orientation, and forms a composite image using image data from the first and from the one or more next x-ray images.

20 Claims, 14 Drawing Sheets

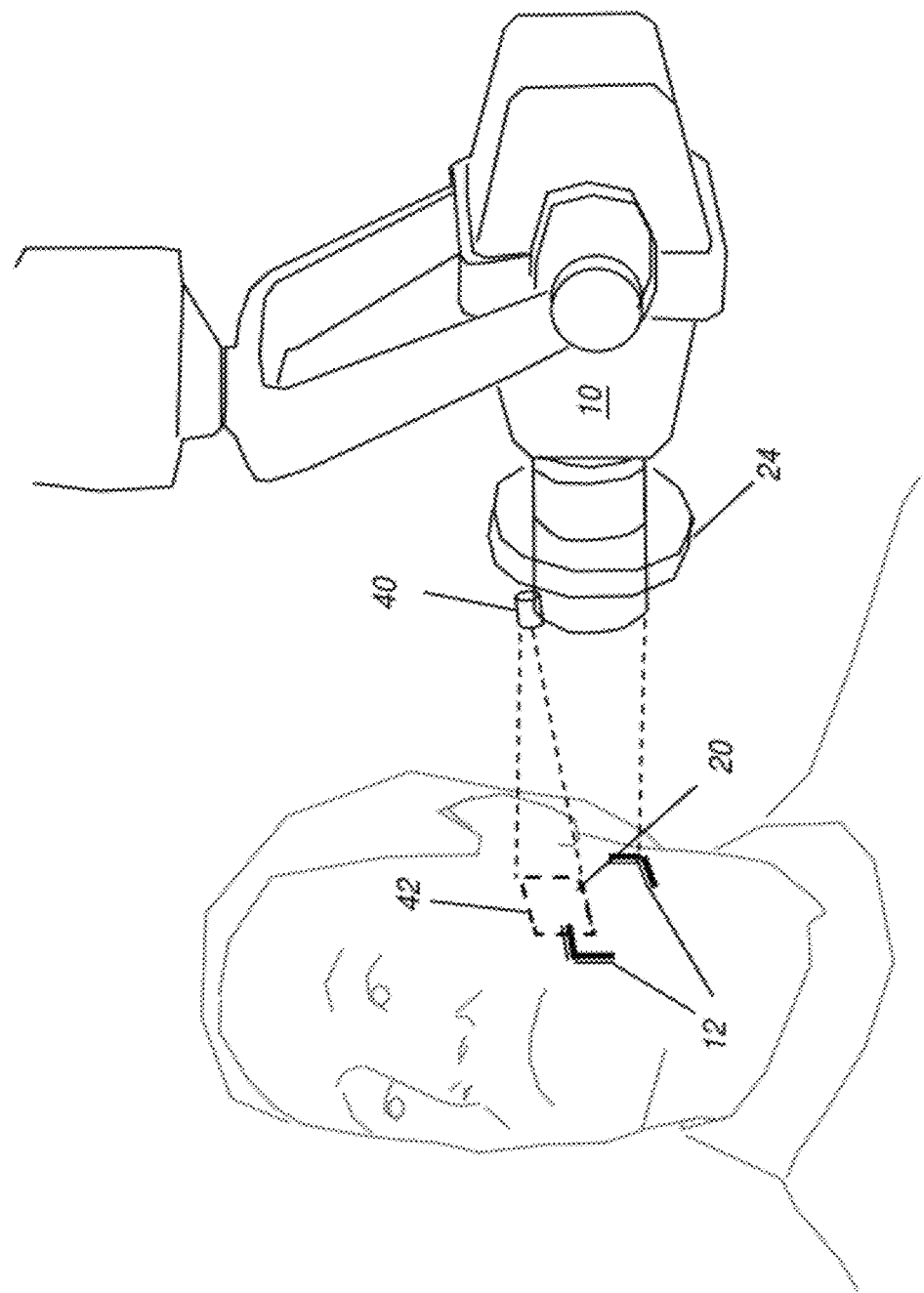

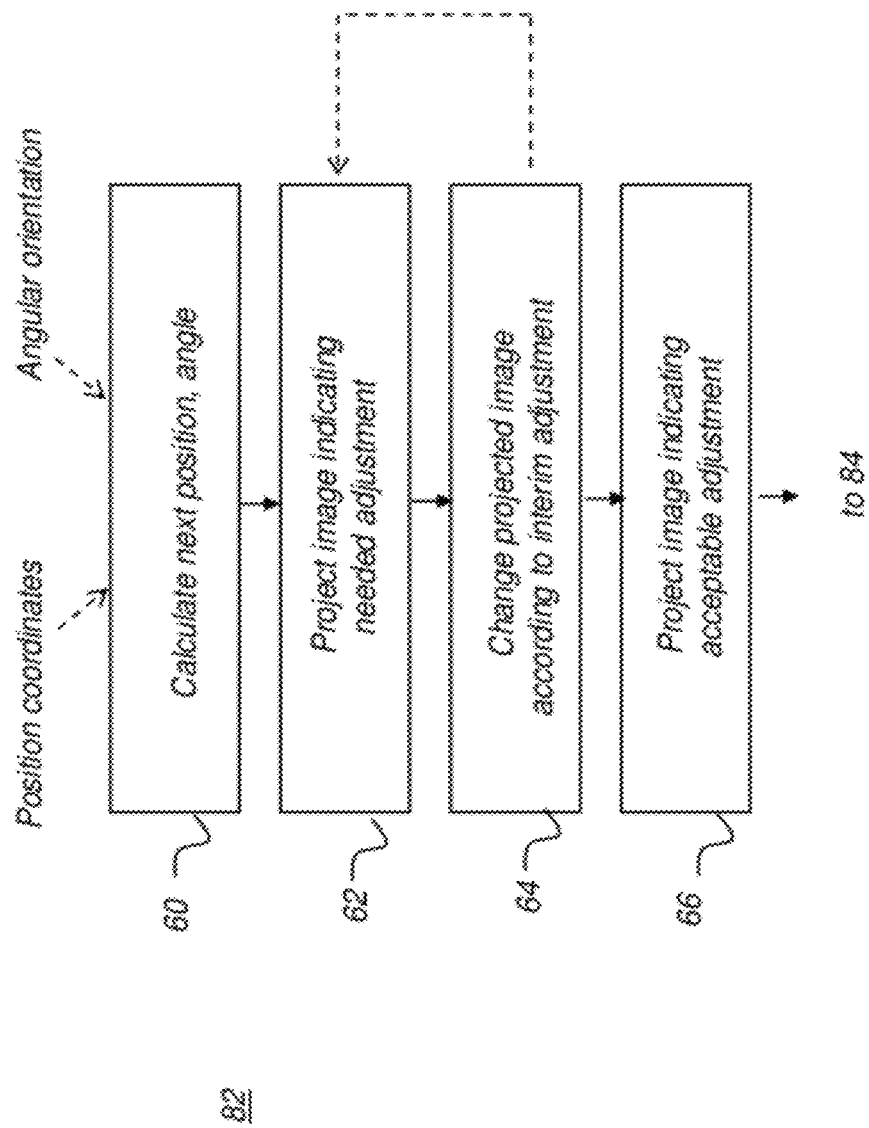

METHOD FOR GENERATING AN INTRAORAL VOLUME IMAGE

FIELD OF THE INVENTION

The invention relates generally to diagnostic imaging and more particularly to an apparatus and method for obtaining multiple intraoral x-rays of a tooth to generate a 3D image representative of the tooth volume.

BACKGROUND OF THE INVENTION

A 3-dimensional (3-D) or volume x-ray image can be of value for diagnosis and treatment of teeth and supporting structures. A volume x-ray image for this purpose is formed by combining image data from two or more individual 2-D projection images, obtained within a short time of each other and with a well-defined angular and positional geometry between each projection image and the subject tooth and between each projection image and the other projection images. Cone-Beam Computerized Tomography (CBCT) is one established method for obtaining a volume image of dental structures from multiple projection images. In CBCT imaging, an image detector and a radiation source orbit a subject and obtain a series of x-ray projection images at small angular increments. The information obtained is then used to synthesize a volume image that faithfully represents the imaged subject to within the available resolution of the system, so that the volume image that is formed can then be viewed from any number of angles. Commercially available CBCT apparatus for dental applications include the Kodak 9500 Cone Beam 3D System from Carestream Health Inc., Rochester, N.Y.

While CBCT imaging is a powerful diagnostic tool, however, there can be cases where, even though volume imaging is beneficial, the full-fledged capability of CBCT imaging is not needed. This has been acknowledged, for example, in disclosures of U.S. Patent Application Publication No. 2007/0127801 entitled "Method for Limited Angle Tomography" by Kalke and U.S. Pat. No. 7,269,241 entitled "Method and Arrangement for Medical X-ray Imaging and Reconstruction from Sparse Data" to Siltanen et al. For some types of volume imaging, such as for use in guiding implant placement, for example, a rudimentary volume imaging capability would be useful. Volume imaging can also help to avoid superposition anomalies between adjacent dental structures. For uses such as these, numerous x-ray projection images, such as those provided from a CBCT system would not be required. Instead, enough volume information can be obtained using a smaller number of x-ray images, provided a spatial coordinate reference between images is maintained.

As a general principle, it can be advantageous to obtain the minimum number of x-ray exposures needed in order to obtain the volume diagnostic data. A complete CBCT series of projection images over a 180 degree orbit employs higher cumulative radiation dosage than does a partial series that is either taken over a smaller range of angles or uses fewer projection images taken at increased relative angular increments. Thus, the methods taught in the '7801 Kalke and '241 Siltanen et al. disclosures can help to reduce patient exposure where full CBCT imaging is not needed.

CBCT systems used for this purpose have both advantages and drawbacks. CBCT equipment maintains the radiation source and sensor at the correct geometry relative to the subject so that an accurate 3-D volume representation is possible. Unless the angular and spatial positioning of source and detector are precisely controlled, any attempt at volume imaging is not likely to provide reliable and precise results. Cost and availability of CBCT equipment, however, are other factors to consider. The CBCT gantry for dental imaging is more expensive than conventional digital x-ray equipment and may not be readily available at a particular treatment site. Significantly, the CBCT system is not usable in an operative or treatment setting, with the patient seated for treatment in the dental chair. Instead, the CBCT image series is obtained in a separate environment that is specifically set up for that purpose.

Commonly assigned patent application number PCT/FR10/00370 entitled "ALIGNMENT APPARATUS FOR DENTAL INTRAORAL RADIOGRAPHY" by Inglese et al., incorporated herein by reference, relates to obtaining suitable alignment between an x-ray source and detector for intraoral radiography, to enable intraoral imaging at an established alignment position. It would be advantageous to be able to use the alignment utilities described therein to help facilitate some level of volume imaging, without the disadvantages of requiring separate CBCT imaging equipment.

Thus, it can be seen that it would be advantageous to provide a method and apparatus for intraoral imaging that allows image data to be obtained that has the correct geometry and is usable for providing a volume image that can be used for some types of diagnosis and treatment, but does not require a CBCT system.

SUMMARY OF THE INVENTION

An object of the present invention is to advance the art of intraoral radiography by providing apparatus and methods for generating a volume image from a small number of x-ray images obtained by an intraoral imaging detector.

A feature of the present invention is its use of an alignment apparatus in conjunction with one or more detectable elements coupled to the image detector to help coordinate the relative positioning of the radiation source to the patient.

An advantage provided by the present invention is the rapid visualization of adjustment necessary to bring the radiation source and image detector into alignment.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for obtaining an intraoral x-ray image for a patient, the method comprising: determining an initial spatial position and an initial angular orientation of an x-ray source relative to a detector that is disposed within the mouth of the patient; obtaining and storing a first x-ray image from the detector with the x-ray source at the initial spatial position and angular orientation and associating the initial spatial position and angular orientation to the first x-ray image; repeating, one or more times, a sequence of: (i) calculating a next spatial position and a next angular orientation for the x-ray source relative to the detector; (ii) providing information that is indicative of positional adjustment that is between the x-ray source and detector for obtaining a next x-ray image at the next spatial position and the next angular orientation; and (iii) measuring and recording an actual spatial position and angular orientation of the x-ray source relative to the detector and obtaining and storing the next x-ray image obtained at the measured spatial position and angular orientation; and forming a composite image using image data from the first x-ray image and from the one or more next x-ray images.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 5 is a perspective view showing an intraoral x-ray imaging apparatus according to one embodiment, in which alignment is not correct.

FIG. 12 is a logic flow diagram that shows system activity in preparation for each image capture in a sequence.

DETAILED DESCRIPTION OF THE INVENTION

Figure 1A:
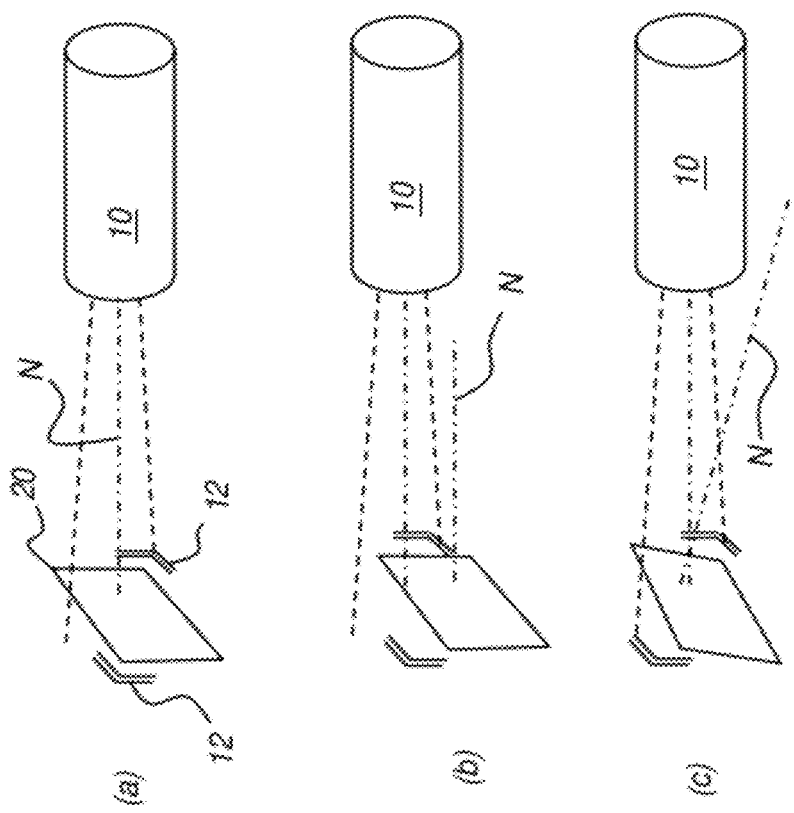
FIGS. 1A and 1B are schematic block diagrams showing different aspects of the alignment problem.

The following is a detailed description of the preferred embodiments of the invention, reference being made to the drawings in which the same reference numerals identify the same elements of structure in each of the several figures.

In the present disclosure, the term "detector" refers to the element that is placed in the patient's mouth, receives radiation, and provides the image content. Such a detector is a digital detector that provides the x-ray image data directly to an imaging system.

Detector alignment can be difficult for dental or intraoral radiography. The detector position is within the patient's mouth and is not visible to the technician. Instead, the technician typically places the detector into some type of holder, and then inserts the holder into place in the mouth. The holder may have a bite plate or other type of supporting member that helps to position the detector appropriately. Holders of this type can be cumbersome and uncomfortable to the patient. Holders and other positioning devices are not error-proof, and positioning errors with these devices can mean that the images obtained are not suitable for diagnosis. Poorly aligned detectors can cause problems such as cone cuts, missed apices, and elongation and related angulation or parallax errors, for example. These alignment problems can result in re-takes, additional image captures to acquire an acceptable image. Re-takes are undesirable due to the additional x-ray radiation exposure to the patient and prolonged patient discomfort with the sensor in the mouth.

Conventional x-ray sources have included aim indicators that help the technician adjust the position and angle of the x-ray source. Often these aim indicators use visible light to trace an outline that helps to center the radiation beam. These are suitable where the radiation detector can be seen, but may not be suitable where the detector is not visible, such as with intraoral imaging. The technician would guess or estimate both the position of the intraoral sensor and the angle of incidence of x-rays on the sensor.

Figure 1B:
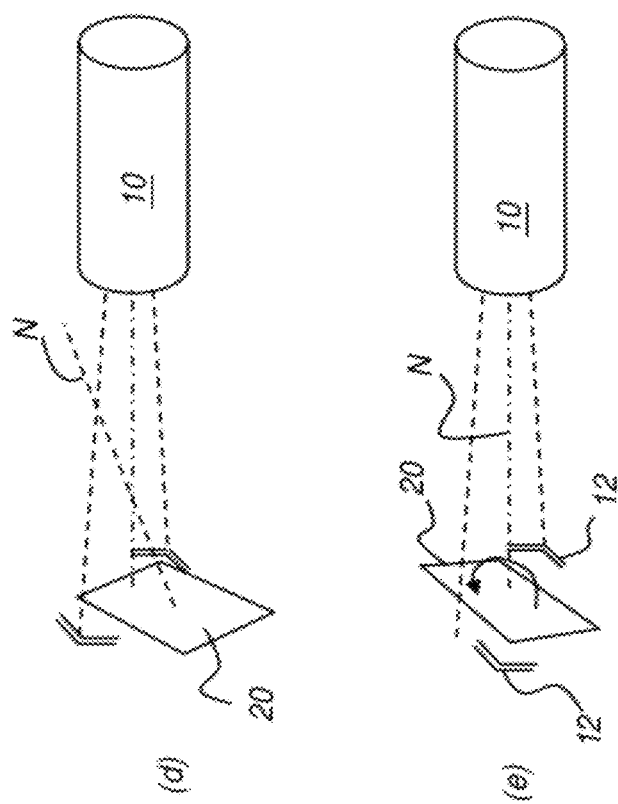

The simplified schematic of FIGS. 1A and 1B show how mis-alignment between an x-ray source 10 and a detector 20 can occur. In these examples, x-ray source 10 provides visible light aim indices 12 used for aim centering. When correct aim alignment is achieved, shown at example (a), detector 20 is centered, as shown within aim indices 12. Aim is incorrect at examples (b) and (d).

For preferred imaging results, proper alignment with respect to angle, or angulation, is desired. Incident radiation from x-ray source 10 is preferably orthogonal to detector 20 as shown in example (a). Line N in FIG. 1 indicates a normal, or orthogonal line, to the surface of detector 20. Examples (c) and (d) show incorrect angular alignment. In example (c), aim is correct but angulation is incorrect. In example (d), both aim and angulation are incorrect. In example (e), detector 20 is rotated in plane.

It is instructive to note that the schematic examples of FIGS. 1A and 1B assume an orthogonal positioning of x-ray source 10 to detector 20. In some embodiments, an oblique orientation may be used.

As the simplified schematic of FIGS. 1A and 1B showed, lateral (side-to-side) position of detector 20 and angulation of the detector 20 inside the patient's mouth are factors related to achieving good alignment. Rotation of the detector within its plane (that is, rotation about orthogonal axis N) is shown at (e) in FIG. 1B, but can be a consideration for maintaining the desired alignment.

Alignment and positioning are suited for volume imaging applications in which images taken at different angles are to be combined in some way to form volume image data.

In order to better understand the parts and operation of the apparatus of the present invention, it is helpful to show how proper alignment can be detected by an imaging system. Referring to the block diagram of FIG. 2, there is shown an intraoral imaging apparatus 22 that detects alignment of imaging detector 20 with x-ray source 10.

Figure 2:
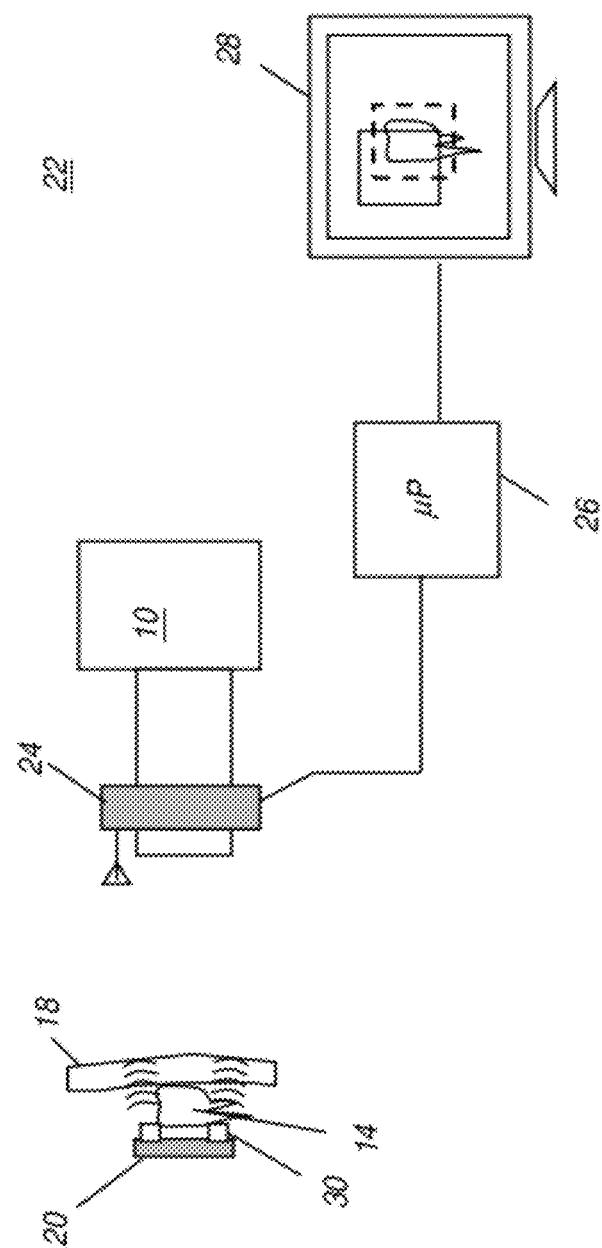
FIG. 2 is a schematic block diagram showing an imaging apparatus that calculates the lateral position and angular orientation of an intraoral image detector.

In the FIG. 2 arrangement, detector 20 is placed at a detector position that is adjacent to a tooth 14, inside a cheek 18 of the patient. Incorporated as part of detector 20 are a number of detectable elements 30, which are shown as electromagnetic signal emitters, such as radio-frequency (RF) emitters. Detectable elements 30 are typically spaced apart from each other in order to provide triangulation information. A sensor 24, itself aligned and positionally coupled with x-ray source 10, senses the presence of detectable element 30 in some way, such as by sensing emitted RF signals. Methods for energizing and sensing RF emitters, such as the tiny emitters used in RFID tags, for example, are known to those in the signal detection arts. A control logic processor 26, in signal communication with one or more sensors 24, employs conventional trigonometric calculations based on the received signals from, or other detectable features of, detectable elements 30 and the known position of sensor 24 with relation to x-ray source 10. This is performed to determine the corresponding positional and angular alignment of detector 20 in the patient's mouth relative to x-ray source 10. An operator console display 28, a computer display monitor, then indicates alignment information for the operator and may recommend the needed adjustment settings. Sensors 24 are energizable to receive electromagnetic signals of one or more predetermined frequencies.

Embodiments of the present invention promote the basic system of FIG. 2 by providing alignment information to the technician where it can be more easily used, particularly where this information is needed to obtain the individual images used for forming a volume image. The alignment apparatus of the present invention projects an image onto the cheek or other portion of the dental patient as a guide for proper alignment of the x-ray tube with respect to the position and angle of the detector.

Figure 3:
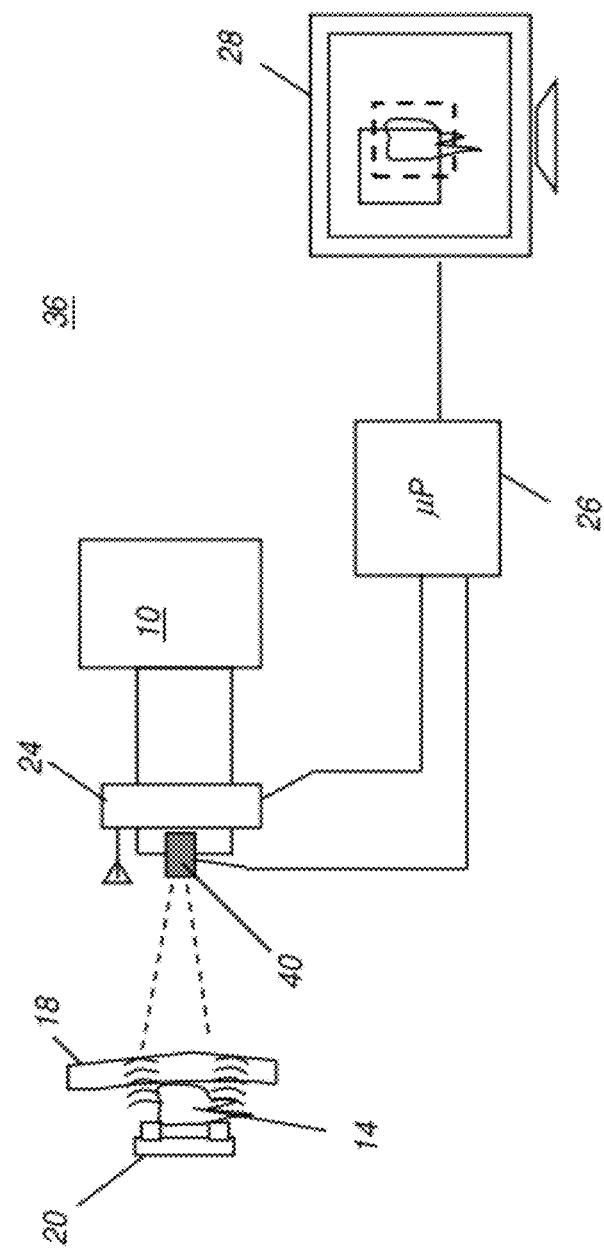
FIG. 3 is a schematic block diagram showing an imaging apparatus that calculates the lateral position and angular orientation of an intraoral image detector and projects a display onto the patient's cheek.

Referring to an embodiment of an imaging apparatus 36 in FIG. 3, control logic processor 26 obtains alignment information in similar manner to that described in FIG. 2. In addition, control logic processor 26 is also in image data signal communication with a projector 40 for projecting an image onto the patient's cheek 18, lips, or face.

Figure 4A:
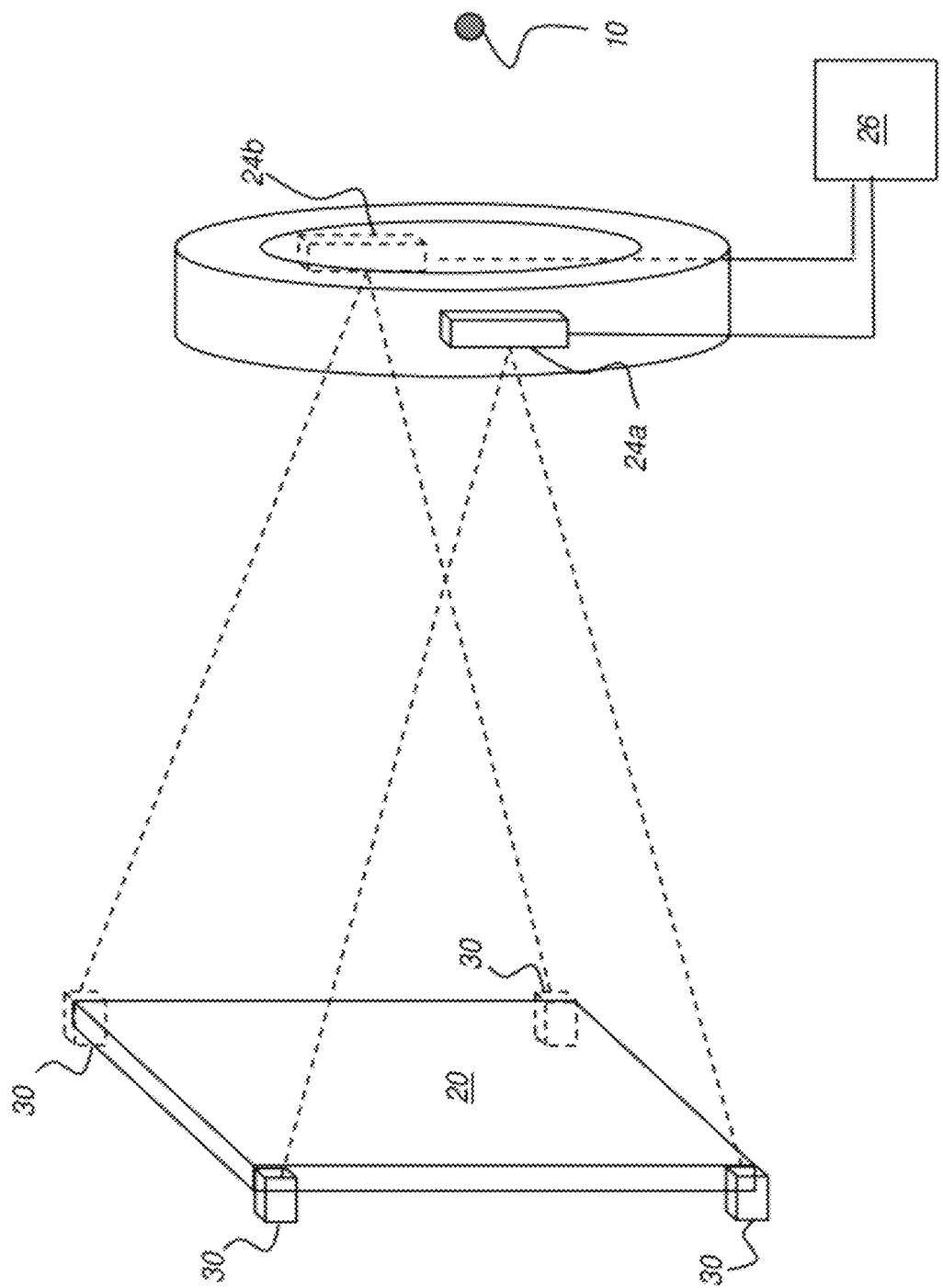
FIG. 4A is a schematic diagram that shows how triangulation is used for position detection in one embodiment of the present invention.

The perspective view of FIG. 4A shows, in schematic form, how triangulation is used to indicate position and angle of detector 20 in order to determine alignment offset in one embodiment. Sensors 24a and 24b, RF transceivers in one embodiment, are at a known position relative to the x-ray source 10, such as mounted near the x-ray source on the x-ray tube, for example. Signal emitters or other type of detectable elements 30 are typically disposed in pairs, positioned at corners of detector 20. Each detectable element 30 has a detectable feature that can be sensed by sensors 24a and 24b. In one embodiment, each detectable element 30 is an RF device that generates an electromagnetic field, such as in response to a transmitted signal from its corresponding signal receiver, sensors 24a or 24b. Phase, intensity, or other characteristic of the emitted electromagnetic field is measured at the corresponding sensors 24a and 24b, and is used in order to determine relative distance between emitting and receiving components. For the RF detection embodiment of FIG. 4A, for example, when signals for each pair of emitters, acting as detectable elements 30, are in phase, good alignment has been achieved. An out-of-phase condition indicates poor alignment and can indicate the needed direction for adjustment. Sensors 24a and 24b are in signal communication with control logic processor 26.

In a similar manner, relative signal strength could alternately be used to indicate the position and angle of detector 20 with respect to the x-ray source for determining alignment offset. Using this approach in an RF embodiment, the nearest signal emitter acting as detectable element 30 has, correspondingly, the strongest intensity signal at sensor 24a or 24b. When the arrangement of FIG. 4A is used, signals of equal intensity emitted from all four emitters or other type of detectable element 30 indicate good alignment. When signal intensities vary, the pattern for their variation can be used to indicate which adjustments are needed.

As one example, U.S. Patent Application Number 2009/0060145, entitled "Positioning Adjustment of a Mobile Radiology Facility" by Tranchant et al., describes a position detection system that uses triangulation and sensing of multiple emitted signals to compute alignment positioning.

It can be appreciated that any of a number of different configurations can be used for determining proper alignment using one or more sensors 24 and detectable elements 30, as is known to those skilled in the signal processing and position sensing arts.

Figure 4B:
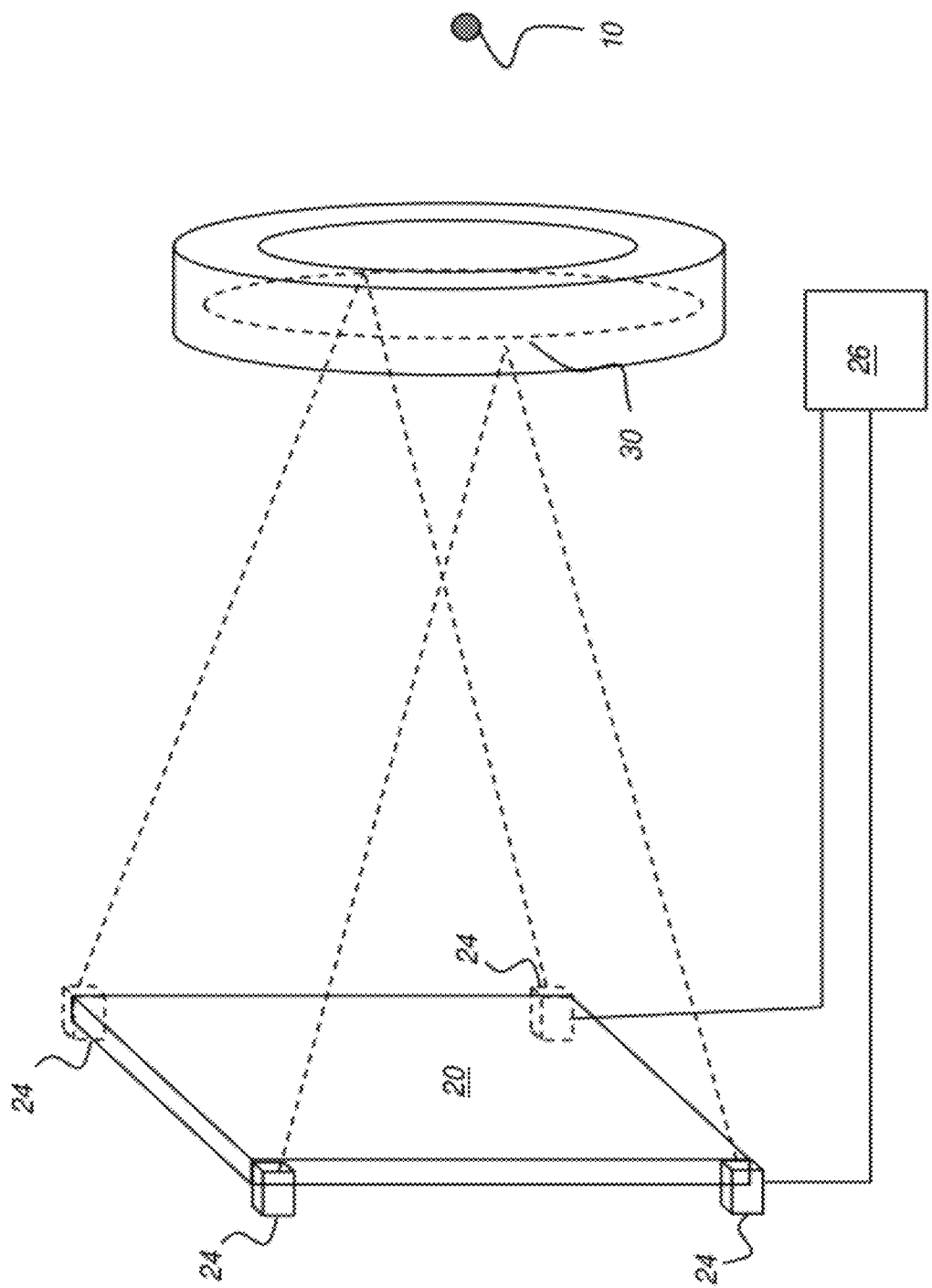
FIG. 4B is a schematic diagram that shows position detection in an alternate embodiment of the present invention.
Figure 6:
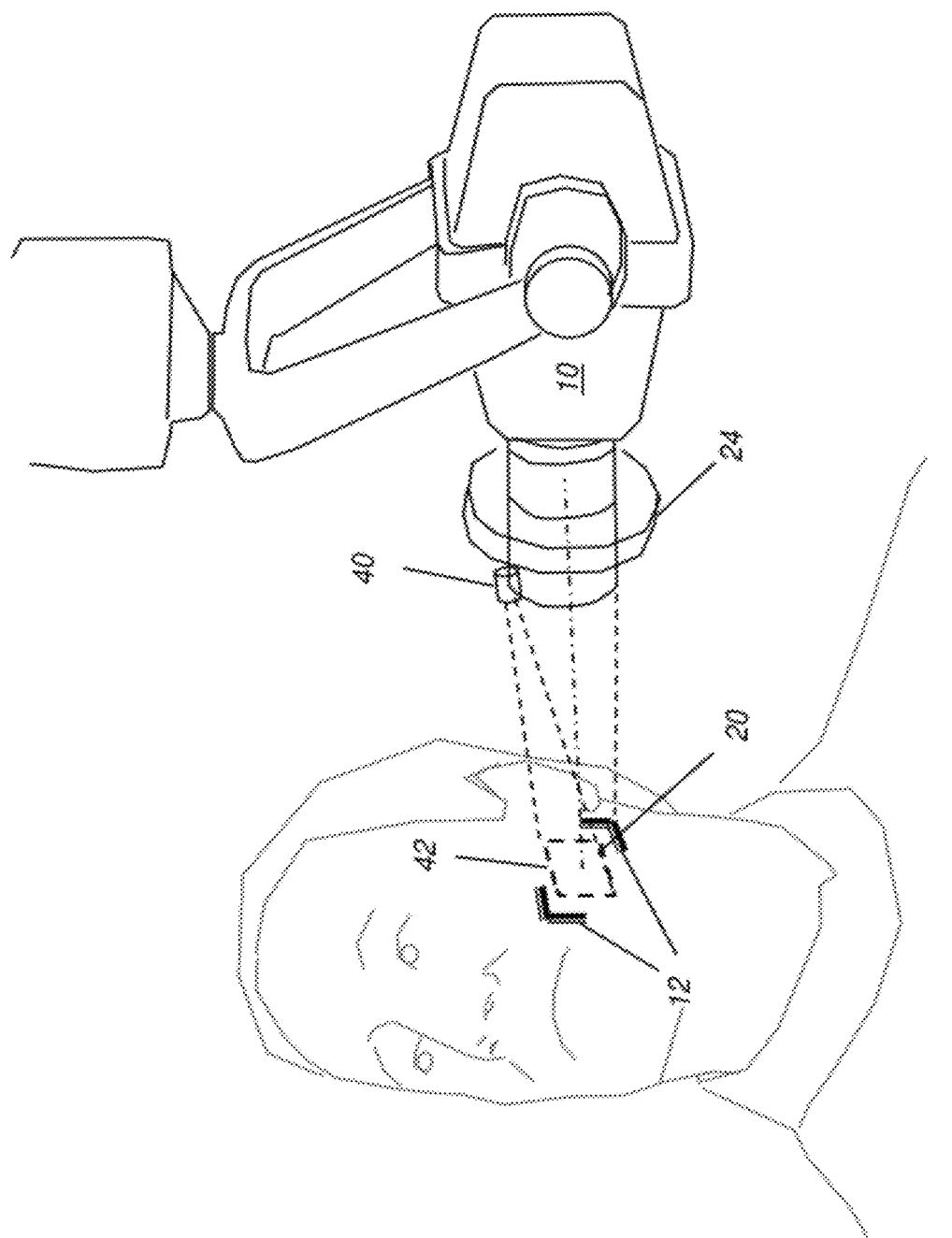
FIG. 6 is a perspective view showing an intraoral x-ray imaging apparatus according to one embodiment, in which alignment is correct.

In one alternative embodiment, shown in FIG. 4B, the emitter-detector arrangement shown in FIG. 4A is reversed, so that one or more emitters that provide one or more detectable elements 30 are mechanically coupled to x-ray source 10 and two or more sensors 24 are attached to detector 20. In the embodiment shown in FIG. 4B, for example, detectable element 30, shown in dashed outline, is a coil that generates an electromagnetic field that is sensed by sensors 24. Sensors 24 are in signal communication with control logic processor 26, either through a wired or a wireless connection Referring to the perspective views of FIGS. 5 and 6, the added advantage of embodiments of the present invention that provide optional image projection is shown. Projector 40, positionally coupled to x-ray source 10, such as mounted in position toward the end of the x-ray tube or on some other portion of the x-ray system, for example, projects a two-dimensional image onto the patient's cheek in order to indicate a position 42 of the concealed detector 20 (shown in dotted outline) and, unless already provided by the x-ray source 10, also to indicate the aim indices 12 of the x-ray source. FIG. 5 shows an example in which aim alignment is incorrect, since position 42 is not aligned with aim indices 12. FIG. 6 shows an example in which aim alignment is correct, with position 42 centered between aim indices 12.

Projector 40 can be any of a number of types of imaging projector that can be mounted onto x-ray source 10. In one embodiment, projector 40 is a pico-projector, such as a Pico Projector Display from Microvision Inc., Redmond, Wash., USA, for example. Devices such as these are advantaged for a number of reasons, including small size, low weight, and low power requirements. These pico-projectors, used in cell-phone and other highly portable electronic devices, scan one or more low-power lasers onto a display surface. The pico-projector employs a minimum of optical components for projection over a range of distances. The laser itself is turned on and off as needed, so that power is consumed only for those image pixels that are projected. This allows the pico-projector to operate at low power levels, so that battery power could be used for projector 40. Alternate embodiments use other types of electronic imaging projectors, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device.

Where lasers are used as illumination sources in projector 40, additional measures can be taken to minimize incidence of coherent laser light to the eyes of the patient or practitioner. Low or very low power lasers can be used, such as solid-state lasers, at scanning rates that deliver only a very small amount of light intensity at any point. A diffusive element may be provided in the light path, for example, to provide some scattering of the laser light, reducing intensity with little or no effect on the quality or utility of the projected image. Light-emitting diodes (LEDs) or other low-power solid-state illumination sources could alternately be used, such as organic LED (OLED) devices.

The image that is projected by projector 40 can have image content that is any of a number of forms and may include both aim indicia 12 for the x-ray source and position 42 indicator for detector 20. Alternatively, where aim indicia 12 are already provided by the x-ray system, projector 40 may only provide a projection showing position 42. Because projector 40 employs a two-dimensional imaging device, the displayed image can have multiple parts and may include additional text fields, direction markers, and other elements. Position 42 may be shown in outline form, as shown in FIGS. 5 and 6, or may be represented in some other way. In one embodiment, the value of angular offset of detector 20 is indicated on the patient's cheek as a displayed numerical message. Alternately, animation or other capabilities of projector 40 could be used to provide, as image content, additional position and angle information.

Color can be used to help indicate the relative amount of alignment offset in various ways. For example, even with the outline of detector 20 projected on the cheek surface, it can be difficult for the technician to know how to adjust for angular alignment. Display of indicia 12 and position 42 in different colors can help to guide the technician in adjusting the angle of the x-ray tube until both aim indicia 12 and position 42 display in the same color, for example. Blinking of the display or of different portions of the displayed elements can also help to indicate and guide alignment adjustments. An audible beep may be provided to indicate acceptable or unacceptable alignment. Stationary indicators, such as arrows or target symbols can be projected as image content onto the cheek of the patient. Animation can be provided to guide adjustment.

Limited-Angle Volume Imaging

The alignment apparatus that is provided by the triangulation sensing apparatus of FIG. 4A or 4B can also be used to assist in capturing a series of images of the same tooth or other structure, taken in quick succession and each at a slightly different angle, for forming a limited-angle volume image. As noted in the background section given previously, this type of volume imaging can have diagnostic value and advantages over a single x-ray image, but without requiring the expense and dose requirements of full-fledged CBCT imaging. In addition, unlike with CBCT imaging, the limited-angle volume image can be acquired with the patient seated in the treatment chair.

Figure 7:
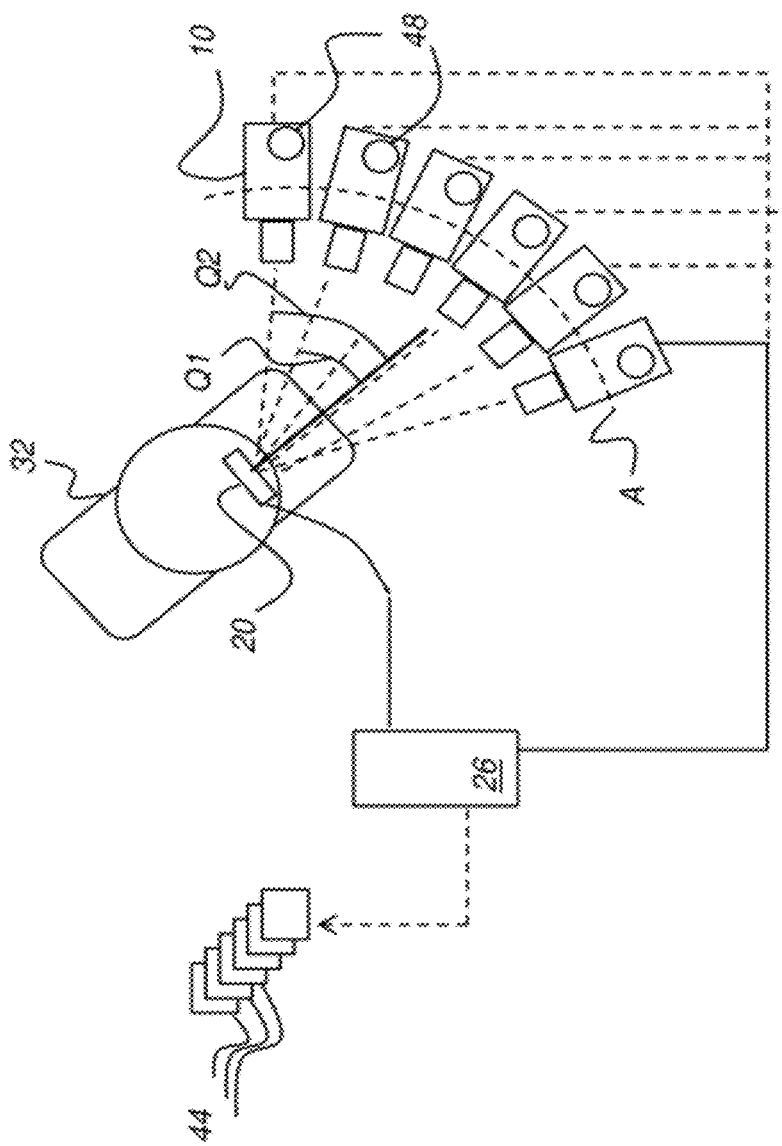
FIG. 7 is a schematic block diagram that shows an imaging pattern used for obtaining a volume image from a limited number of x-rays.

Referring to FIG. 7, there is shown, from a top view, a schematic block diagram of an imaging pattern used for obtaining a limited-angle volume image from a patient 32 using a limited number of x-rays and a digital detector. X-ray source 10 is used to direct exposure to detector 20 from a number of angular orientations, shown as capture or exposure angles in FIG. 7, along an arcuate path A. At each of two or more exposure angle positions, with two called out by way of example as angles Q1 and Q2 in FIG. 7, radiation energy is directed to detector 20 and the corresponding image data from the digital detector obtained by control logic processor 26 and stored as a component image 44, indexed according to the relative acquisition geometry for the image, such as by the exposure angle orientation. In this way, one component image 44 is obtained and stored for each exposure angle. Control logic processor 26 can then generate a volume image as a composite image, using the combined data from the individual component images 44.

Additional sensing components and logic associated therewith are used to provide positional and angular information about each image that is obtained. In one embodiment, for example, fixed positional and angular coordinates are assigned to an initial spatial position and angular orientation of X-ray source 10. Then, system logic records the changed position and angle that correspond to each imaging position in the series of images that are obtained. This data then provides the needed reference geometry for reconstruction of the 3-D volume image from a series of 2-D image captures. Spatial position data can be obtained in a number of ways, such as using an angular sensor 48 that is coupled with a gantry or other transport apparatus that is used for movement of x-ray source 10, for example.

In order for this type of limited-angle volume imaging to work correctly, the angular orientation and spatial arrangement of X-ray source 10 relative to detector 20 is known for each image throughout the imaging cycle, so that the component data that is obtained can be properly aligned and correlated. For the embodiment shown in FIG. 7 and in the perspective view of FIG. 8, the head of patient 32 and spatial position of detector 20 (shown in dashed outline in FIG. 8) are rigidly fixed in position while X-ray source 10 is moved orbitally from one relative angular orientation to the next. It may be desirable to mechanically fix the spatial position of detector 20 relative to the subject that is being imaged. With respect to FIGS. 7 and 8, for example, one or more bite blocks or a clip-on device may be useful for rigidly fixing detector 20 at a position within the mouth of patient 32.

Data is obtained in order to identify the spatial position of detector 20 and the relative spatial position of X-ray source 10 for each image. In the alternate embodiment of FIG. 9, X-ray source 10 is fixed in place and patient 32 is rotated, such as by incrementally rotating a treatment chair for example, to shift from one exposure angular orientation to the next. Again, relative positional information for both detector 20 and X-ray source 10 is established and stored for each component image by control logic processor 26 or a related processing device.

It can be appreciated that control logic processor 26 obtains and stores both image data and positional information when performing this type of imaging. As each image is obtained, control logic processor 26 stores the image data and corresponding information about the relative spatial position of the x-source and detector 20. Position data and image data can be stored as part of the same data structure, such as in the image data file, or may be stored in separate data structures, such as in separate files or database locations. In one embodiment, control logic processor 26, then optionally provides information that indicates a recommended positional adjustment for the x-ray source for obtaining the next x-ray image at the next spatial position and the next angular orientation. This information on recommended positional adjustment can be provided in a number of ways, including displayed information on display 28 (FIG. 3), using an audible cue, or by providing graphical guidance to the operator in order to set up the next exposure, which can be in the form of projected image content and format, such as by projecting instructions or target information onto the cheek of the patient, for example. Relative positional information related to each image is stored in some form and used by image processing logic on control logic processor 26 in order to generate the volume image.

In one embodiment, the projected image from projector 40 (FIG. 6) instructs the technician on how to re-aim X-ray source 10 or how to adjust the position of the treatment chair in order to set up for the next image in the sequence. Projected color, patterning, alphanumeric text, animation, flashing or blinking, or other mechanism can be used to guide positioning adjustment between image captures.

Figure 10:
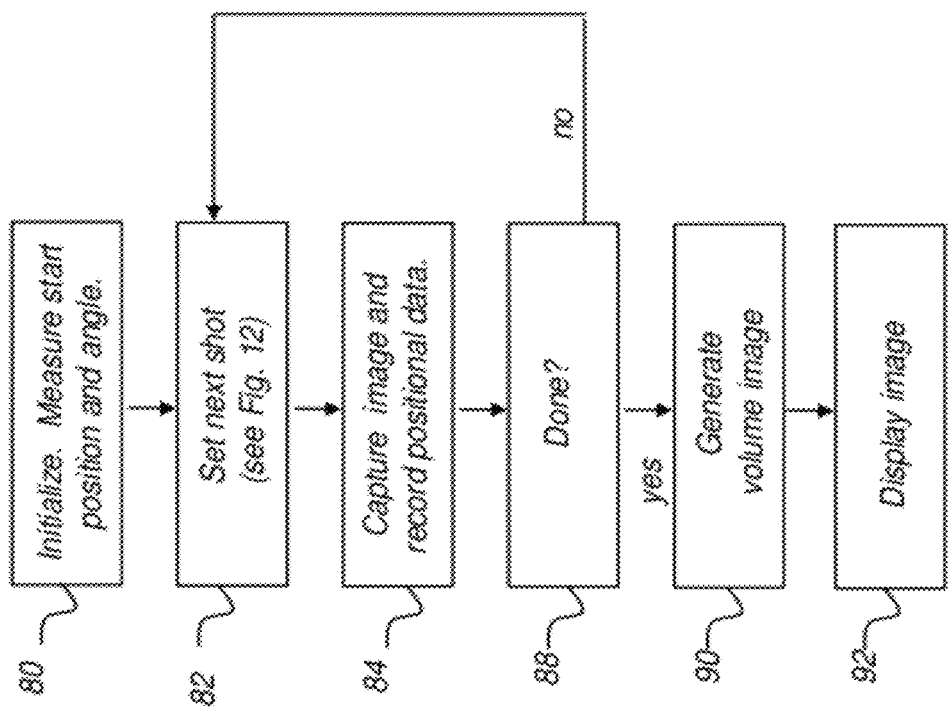
FIG. 10 is a logic flow diagram that shows a sequence for capturing x-ray images to generate a volume image.

The logic flow diagram of FIG. 10 shows a sequence of steps for obtaining a series of component images in one embodiment. An initialization step 80 begins the sequence and obtains data on the initial start position and angle. In one embodiment, initialization step 80 also sets up or calculates the number of images to be obtained and, for each image, its corresponding exposure angle. This information may be fixed or variable, and may be calculated using control logic processor 26 or entered by the dentist or technician using setup software that is in communication with control logic processor 26. Detector 20 is securely positioned in the patient's mouth and the source-detector alignment is at least coarsely made by the technician. In a setup step 82, imaging apparatus 22 provides the image display, projected onto the face or head of the patient, to help guide alignment and aim of X-ray source 10, as was described earlier with reference to FIGS. 5 and 6. In one embodiment, the image content that is projected onto a portion of the patient changes according to the relative accuracy of the angular orientation. This can be a change in color, intensity, blinking, or other attribute of the projected content. It is noted that the display may provide a hint or suggestion of the preferred/best position for each subsequent radiographic image capture. However, it is desirable that the actual spatial position be accurately measured and recorded in order for proper execution of the limited-angle volume imaging algorithms.

Continuing with the logic flow of FIG. 10, each component image is obtained in an image capture step 84, and the image stored along with information about the actual measured spatial position and the angular orientation at which the exposure was obtained. A decision step 88 checks to determine whether or not all component images utilized according to initialization step 80 have been obtained and loops back to setup step 82 when subsequent images are utilized. At the conclusion of this processing for image capture, a volume image generation step 90 is executed in order to generate the resulting composite volume image obtained from this sequence. A display step 92 then displays the volume image that has been generated.

Figure 11:
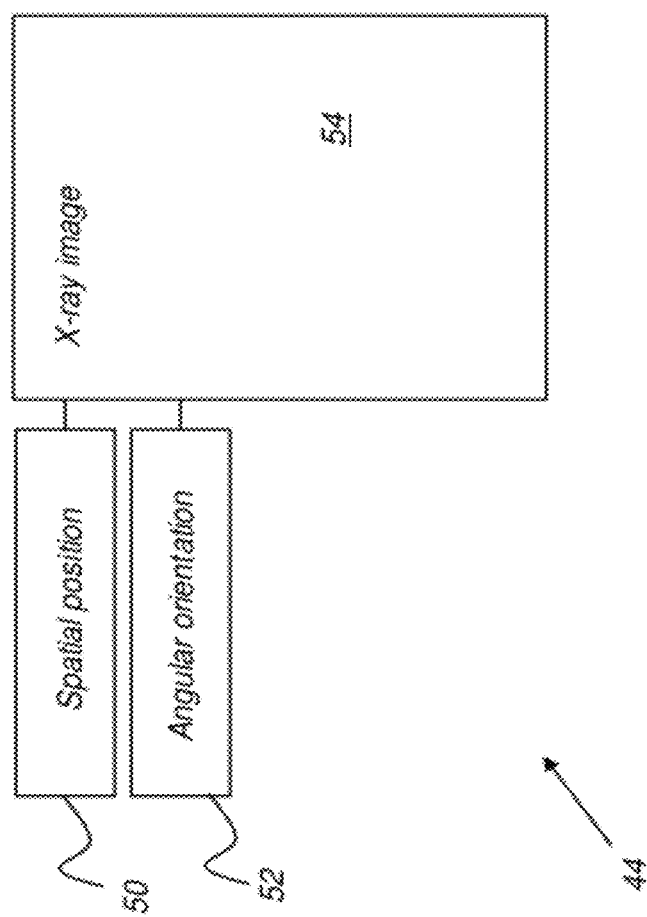
FIG. 11 is a block diagram showing spatial position and angular orientation information associated with the image data.

FIG. 11 is a block diagram showing spatial position and angular orientation associated with the image data for each component image 44 in the set of images that is obtained. In the embodiment shown, a spatial position data field 50 and an angular orientation data field 52 are stored along with x-ray image data 54, such as by storing the measured position and angle geometry in a header portion of the x-ray image data file. Alternately, spatial position and angular orientation data can be separately stored, linked or otherwise associated with the image data. This information is employed for proper reconstruction of the volume image.

FIG. 12 is a logic flow diagram that shows optional system activity within image setup step 82 of FIG. 10 in preparation for each image capture in a sequence. A calculation step 60 uses position coordinate and angular orientation data from the x-ray system or stored with the previous image and calculates a next position and angular orientation for relative movement of x-ray source 10 and/or detector 20. An optional target projection step 62 then projects an image onto the patient, wherein the image is indicative of positional adjustment and angular adjustment that is between x-ray source 10 and detector 20 for obtaining a next x-ray image at the next spatial position and angular orientation. As noted earlier, the optional projected display can indicate the needed adjustment using color, blinking or other effects, numeric values, directional indicators or icons, such as an arrow, or other visual effects. Then, in a looping operation, a reassessment step 64 periodically readjusts the projected display according to measured changes in positional adjustment and angle that have been made by the technician. When adjustment is correct to within some predetermined tolerance, a correct adjustment display step 66 then executes, indicating that the adjustment is acceptable for obtaining the next image.

Figure 8:
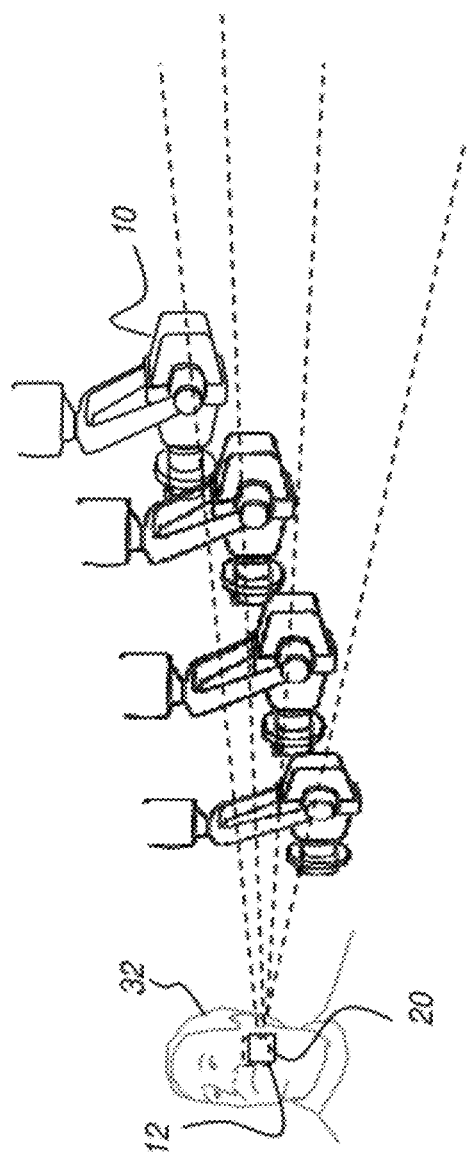
FIG. 8 is a perspective view showing how different positions of the x-ray emitter relative to the patient provide individual images for use in forming a volume image.
Figure 9:
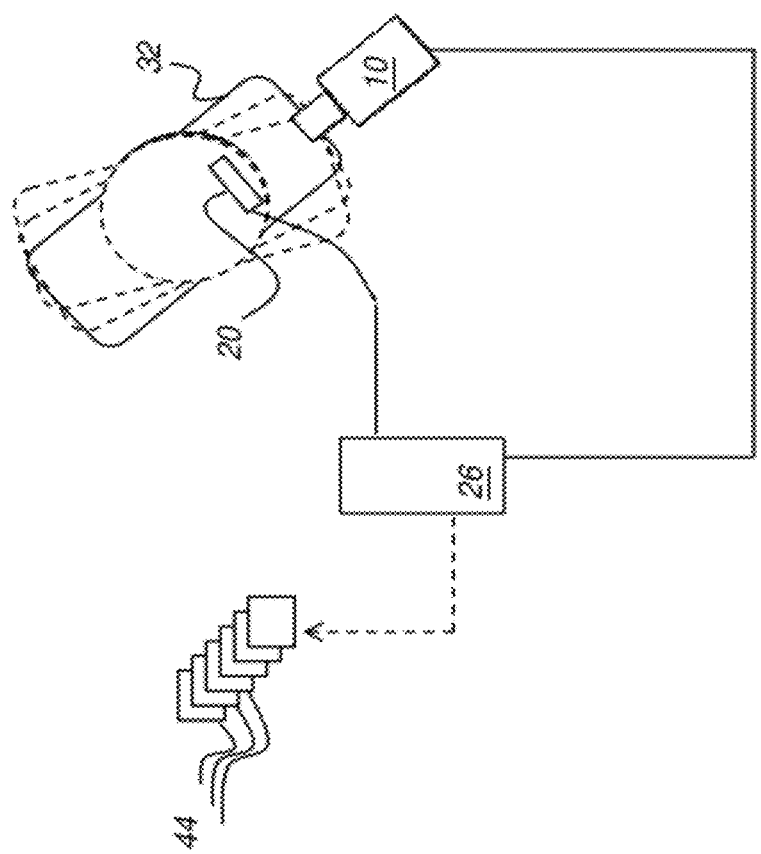
FIG. 9 is a schematic block diagram that shows an imaging pattern used for obtaining a volume image from a limited number of x-rays in an alternate embodiment.

Given the information that is available on relative position when using the component arrangement shown in FIGS. 7-9, an embodiment of the present invention uses continual re-calculation and repeated checks of sensors and other position-sensing components for correction of, and adapting to, minor position changes and patient movement. With this arrangement, it is not necessary that detector 20 and x-ray source 10 have fixed, predetermined positions relative to each other or achieve precisely those positions calculated for the next image. However, in any case, detector 20 has a fixed spatial position relative to the teeth or other objects being imaged. Programmed image processing logic can adapt to changes in position that are within a reasonable range of angles, for example. In one embodiment, one or more additional position sensors at fixed spatial positions are used to establish reference points for angular and positional orientation. In addition, automated detection and correction of patient motion artifacts can also be performed, using image processing techniques known to those skilled in the image acquisition arts.

The limited-angle volume image that is formed from two or more component X-ray images provides some measure of volume-related information for the tooth or other imaged structure. Advantageously, this is provided without the higher levels of exposure needed for full CBCT imaging and without the need for specialized CBCT gantry and related equipment. Positional information that is obtained using sensor 24 and detectable elements 30 is used by 3-D image reconstruction algorithms to generate a corresponding volume image that includes a tooth or other feature and to populate voxels within that volume image with suitable data values. The volume image can be formed without requiring the complex filtered back-projection algorithms that are typically used for CBCT reconstruction, for example. Images obtained can be viewed on a conventional display monitor or may be viewed using a stereoscopic viewing apparatus, for example. The volume image can be generated dynamically according to a preferred viewing angle indicated by the practitioner, for example.

Control logic processor 26 or an associated processor or other computer used for image processing can execute any of a number of known techniques for limited-angle reconstruction, familiar to those skilled in the 3-D imaging arts. For example, in an article entitled "A comparative study of limited-angle cone-beam reconstruction methods for breast tomosynthesis", *Med. Phys.* October 2006; 33(10): pp. 3781-3795, authors Zhang et al. describe a number of reconstruction algorithms used to solve a similar type of problem in limited-angle mammographic imaging, including back-projection, algebraic reconstruction, and probabilistic techniques. The Siltanen et al. '241 patent noted earlier describes a 3-D reconstruction method from sparse 2-D image data using modeling data for tooth structures. The Kalke '7801 application noted earlier describes another method for tooth image reconstruction using a frequency transform. Other reconstruction methods for 3-D imaging could alternately be employed.

Among its advantages, a volume image can be formed for viewing from different angles, depending on how much component image data is available. Where a sufficient number of component images are obtained at different relative angles, the resulting volume image can be formed and displayed from multiple view angles, thus assisting the dental practitioner in making a more accurate diagnostic assessment of a tooth or other structure.

The invention has been described in detail with particular reference to a presently preferred embodiment, but it will be understood that variations and modifications can be effected within the spirit and scope of the invention. For example, control logic processor 26 (FIGS. 2-4, 7, 9) can be any of a number of types of logic processing device, including a computer or computer workstation, a dedicated host processor, a microprocessor, logic array, or other device that executes stored program logic instructions. Control logic processor 26 may also connect to detector 20 for obtaining an image and for controlling the operation of signal emitters 30. The electromagnetic signals emitted and detected for determining position can be any of a number of types of signal, such as RF signals in the 10 kHz-100 MHz range, for example. Projection of an image onto the patient's cheek as shown in FIGS. 5 and 6 is optional, but helps to guide the technician for obtaining the desired imaging geometry. Other methods can be used for providing positional adjustment information to the operator, such as using an on-screen indicator or other indicator device or using an audible signal, for example.

Embodiments shown and described with reference to FIGS. 2 and 3 showed use of radio frequency transmission and reception for identifying the position of intra-oral imaging detector 20. In such an embodiment, detectable element 30 is an RF emitter, such as an RFID device. Alternately, detectable element 30 can emit some other electromagnetic signal, such as light, for example. A bright light source from within the mouth may be perceptible to a sensor, particularly where the light is incident upon less dense tissue, such as the cheek. The light can be from within or outside of the visible spectrum. In yet another embodiment, ultrasound signals are emitted from detectable element 30 and sensed at sensor(s) 24. Yet another embodiment employs magnets as detectable elements 30 and uses magnetic attraction as a guide to determining the position and angular orientation of detector 20 within the patient's mouth.

The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for obtaining an intraoral x-ray image for a patient, comprising:
   determining an initial spatial position and an initial angular orientation of an x-ray source relative to a detector that is disposed within the mouth of the patient;
   obtaining and storing a first x-ray image from the detector with the x-ray source at the initial spatial position and angular orientation and associating the initial spatial position and angular orientation to the first x-ray image;
   repeating, one or more times, a sequence of:
      (i) calculating a next spatial position and a next angular orientation for the x-ray source relative to the detector;
      (ii) providing information that is indicative of positional adjustment that is between the x-ray source and detector for obtaining a next x-ray image at the next spatial position and the next angular orientation; and
      (iii) measuring and recording an actual spatial position and angular orientation of the x-ray source relative to the detector and obtaining and storing the next x-ray image obtained at the measured spatial position and angular orientation; and
   forming a composite image using image data from the first x-ray image and from the one or more next x-ray images.

2. The method of claim 1 wherein providing information that is indicative of positional adjustment comprises projecting an image onto a portion of the patient.

3. The method of claim 1 wherein providing information that is indicative of positional adjustment comprises displaying information on a computer monitor.

4. The method of claim 1 wherein providing information that is indicative of positional adjustment comprises providing an audible cue.

5. The method of claim 1 further comprising displaying the composite image as a volume image.

6. The method of claim 1 wherein the positional adjustment is obtained by moving the X-ray source.

7. The method of claim 1 wherein the positional adjustment is obtained by moving the patient.

8. The method of claim 2 wherein the image that is projected onto the portion of the patient changes according to adjustment of the angular orientation.

9. The method of claim 8 wherein the projected image content changes in one or more of color, blinking, a pattern, an animation, an alphanumeric value display, one or more directional indicators, and one or more icons.

10. The method of claim 1 wherein the measured spatial position and angular orientation are stored in the same data structure that stores the image data.

11. The method of claim 1 wherein the measured spatial position and angular orientation are stored separately from the image data.

12. The method of claim 1 further comprising correcting motion artifacts using the spatial position and angular orientation.

13. The method of claim 1 further comprising fixing the position of the detector within the mouth of the patient.

14. A method for obtaining a volume intraoral x-ray image for a patient, comprising:
   a) calculating a spatial position of an intraoral image detector relative to an x-ray source by detecting the location of one or more detectable elements that are positionally associated with either the intraoral image detector or the x-ray source;
   b) providing information that is indicative of positional adjustment that is between the x-ray source and detector for obtaining a next x-ray image at a next spatial position and at a next angular orientation;
   c) obtaining X-ray image data from the intraoral image detector and storing the image data and associated information relating to a measured position of the X-ray source to the detector;
   d) repeating steps a), b), and c) one or more times for subsequent changes in the relative position of the X-ray source to the detector; and
   e) generating the volume image according to the x-ray image data and information relating to the corresponding measured positions of the X-ray source to the detector.

15. The method of claim 14 wherein providing information that is indicative of positional adjustment comprises projecting a visible image toward the patient according to the calculated detector position, wherein the projected image is a guide for aiming the X-ray source toward the intraoral image detector.

16. The method of claim 15 wherein projecting an image comprises using solid-state illumination.

17. The method of claim 14 wherein detecting the location of one or more detectable elements comprises sensing a radio-frequency signal.

18. The method of claim 14 wherein detecting the location of one or more detectable elements comprises either: (a) sensing an emitted light signal, or (b) sensing a magnet.

19. The method of claim 15 wherein projecting an image comprises using a digital micromirror array or a liquid crystal device.

20. The method of claim 15 wherein the projected image (a) is a color image, or (b) varies in appearance according to an alignment offset between the x-ray source and the intraoral image detector.

* * * * *